(12) United States Patent
Tanaka

(10) Patent No.: US 8,251,890 B2
(45) Date of Patent: Aug. 28, 2012

(54) ENDOSCOPE INSERTION SHAPE ANALYSIS SYSTEM AND BIOLOGICAL OBSERVATION SYSTEM

(75) Inventor: Hideki Tanaka, Tama (JP)

(73) Assignee: Olympus Medical Systems Corp., Tokyo (JP)

( * ) Notice: Subject to any disclaimer, the term of this patent is extended or adjusted under 35 U.S.C. 154(b) by 518 days.

(21) Appl. No.: 12/464,404

(22) Filed: May 12, 2009

(65) Prior Publication Data

US 2009/0221869 A1 Sep. 3, 2009

Related U.S. Application Data

(63) Continuation of application No. PCT/JP2007/063882, filed on Jul. 12, 2007.

(30) Foreign Application Priority Data

| Nov. 13, 2006 | (JP) | 2006-306974 |
| Nov. 13, 2006 | (JP) | 2006-306975 |
| Nov. 30, 2006 | (JP) | 2006-324901 |

(51) Int. Cl.
*A61B 1/00* (2006.01)

(52) U.S. Cl. ......... 600/103; 600/117; 600/118; 600/145

(58) Field of Classification Search .................. 600/101, 600/117–118, 145, 150, 422–424, 103
See application file for complete search history.

(56) References Cited

U.S. PATENT DOCUMENTS

| 5,913,820 | A * | 6/1999 | Bladen et al. ............... 600/407 |
| 6,059,718 | A * | 5/2000 | Taniguchi et al. ........... 600/117 |
| 6,087,831 | A * | 7/2000 | Bornert et al. .............. 324/307 |
| 6,511,417 | B1 * | 1/2003 | Taniguchi et al. ........... 600/117 |
| 6,773,393 | B1 * | 8/2004 | Taniguchi et al. ........... 600/117 |
| 6,876,196 | B1 * | 4/2005 | Taulu et al. ................. 324/247 |
| 2005/0228221 | A1 * | 10/2005 | Hirakawa ................... 600/101 |
| 2007/0197869 | A1 * | 8/2007 | Uchiyama et al. .......... 600/114 |
| 2007/0225550 | A1 * | 9/2007 | Gattani et al. .............. 600/101 |
| 2009/0102479 | A1 * | 4/2009 | Smith et al. ................. 324/309 |

FOREIGN PATENT DOCUMENTS

| EP | 1 504 712 A1 | 2/2005 |
| JP | 2004-358095 | 12/2004 |
| JP | 2006-288752 | 10/2006 |
| WO | WO 2004/039249 A1 | 5/2004 |

\* cited by examiner

*Primary Examiner* — John P Leubecker
*Assistant Examiner* — Arnaldo Torres Diaz
(74) *Attorney, Agent, or Firm* — Scully, Scott, Murphy & Presser PC

(57) ABSTRACT

An endoscope insertion shape analysis system of the present invention includes an insertion state acquisition unit that acquires coordinate values of a plurality of locations in an insertion portion of an endoscope inserted in an examinee, an insertion shape detection unit that detects at least some insertion shapes of the insertion portion inserted in the examinee based on the coordinate values at the plurality of locations, a coordinate plane setting unit that sets a plurality of coordinate planes according to the coordinate values and the insertion shapes at the plurality of predetermined locations, an insertion shape projecting unit that projects the insertion shapes onto the plurality of coordinate planes and an insertion shape judging unit that judges whether or not a predetermined shape exists in the insertion shapes projected onto the plurality of coordinate planes.

6 Claims, 11 Drawing Sheets

INSERTION SHAPE DATA

FRAME DATA

COIL COORDINATES

● ··· FIRST MARKER

× ··· SECOND MARKER

ENDOSCOPE INSERTION SHAPE ANALYSIS SYSTEM AND BIOLOGICAL OBSERVATION SYSTEM

CROSS REFERENCE TO RELATED APPLICATION

This application is a continuation application of PCT/JP2007/063882 filed on Jul. 12, 2007 and claims benefit of Japanese Applications No. 2006-306974 filed in Japan on Nov. 13, 2006, No. 2006-306975 filed in Japan on Nov. 13, 2006, and No. 2006-324901 filed in Japan on Nov. 30, 2006, the entire contents of each of which are incorporated herein by their reference.

BACKGROUND OF THE INVENTION

1. Field of the Invention

The present invention relates to an endoscope insertion shape analysis system and a biological observation system, and more particularly, to an endoscope insertion shape analysis system and a biological observation system capable of acquiring information for assisting insertion operation of an insertion portion of an endoscope.

2. Description of the Related Art

Endoscopes are conventionally widely used in medical and industrial fields or the like. Furthermore, endoscopes in the medical field are used when performing observations and various treatments of living tissue or the like.

Especially when an insertion portion of an endoscope is inserted from the anus of an examinee to perform observations and various treatments of the lower digestive tract, an endoscope insertion shape analysis system capable of detecting the position of the insertion portion in the body cavity and bending condition or the like is used together with the endoscope in order to smoothly insert the insertion portion into the crooked body cavity.

An endoscope insertion shape analyzer is described, for example, in Japanese Patent Application Laid-Open Publication No. 2004-358095 as an apparatus having a function substantially the same as that of the aforementioned endoscope insertion shape detection system.

Japanese Patent Application Laid-Open Publication No. 2004-358095 discloses a configuration in which a portion corresponding to a loop forming candidate of an insertion portion of an endoscope is divided into n portions, three-dimensional coordinate values of each dividing point projected onto a predetermined plane (z=0 plane) are transformed into feature values as P-type Fourier descriptors and the feature values are compared with instructor data to thereby judge whether or not the portion corresponding to the loop forming candidate forms a loop shape.

Furthermore, the endoscope insertion shape analyzer of Japanese Patent Application Laid-Open Publication No. 2004-358095 has a function of judging that the large intestine has stretched when it is detected that a moving distance of a distal end portion of the endoscope inserted in the large intestine within a predetermined period of time is equal to or less than a predetermined threshold and the length of the insertion portion of the endoscope inserted in the large intestine continues to increase.

Furthermore, the endoscope insertion shape analyzer of Japanese Patent Application Laid-Open Publication No. 2004-358095 is configured by including shape analysis means for analyzing the shape of the insertion portion of the endoscope and information providing means for providing information on the shape of the insertion portion according to the analysis result of the shape analysis means. In such a configuration, the endoscope insertion shape analyzer of Japanese Patent Application Laid-Open Publication No. 2004-358095 can provide information that leads to improvement of insertability of the endoscope.

SUMMARY OF THE INVENTION

An endoscope insertion shape analysis system according to a first aspect of the present invention includes an insertion state acquisition unit that acquires coordinate values of a plurality of locations in an insertion portion of an endoscope inserted in an examinee, an insertion shape detection unit that detects at least some insertion shapes of the insertion portion inserted in the examinee based on the coordinate values at the plurality of locations, a coordinate plane setting unit that sets a plurality of coordinate planes according to the coordinate values and the insertion shapes at the plurality of predetermined locations, an insertion shape projecting unit that projects the insertion shapes onto the plurality of coordinate planes and an insertion shape judging unit that judges whether or not a predetermined shape exists in the insertion shapes projected onto the plurality of coordinate planes.

An endoscope insertion shape analysis system according to a second aspect of the present invention includes an insertion shape detection unit that detects an insertion shape of an insertion portion based on coordinate values of a plurality of locations of the insertion portion of an endoscope inserted in an examinee, an insertion shape dividing unit that generates a line segment according to the insertion shape and sets a plurality of dividing points on the line segment and an insertion stop point estimation unit that detects whether or not insertion operation is performed on the insertion portion based on a moving speed on a proximal end side of the insertion portion and detects one dividing point out of the plurality of dividing points where a coordinate value on a predetermined coordinate axis locally becomes maximum and a transmission rate of the moving speed that varies according to the insertion operation is less than a predetermined threshold.

An endoscope insertion shape analysis system according to a third aspect of the present invention includes an insertion shape detection unit that detects an insertion shape of an insertion portion based on coordinate values of a plurality of locations of the insertion portion of an endoscope inserted in an examinee, an insertion shape dividing unit that generates a line segment according to the insertion shape and sets a plurality of dividing points on the line segment and an insertion stop point estimation unit that detects whether or not insertion operation is performed on the insertion portion based on a moving speed on a proximal end side of the insertion portion and detects one dividing point out of the plurality of dividing points where a coordinate value on a predetermined coordinate axis locally becomes maximum and a local radius of curvature that varies according to the insertion operation is less than a predetermined threshold.

A biological observation system of the present invention includes an insertion state acquisition unit that acquires insertion state information, which is information including coordinate values of a plurality of predetermined locations in an insertion portion of an endoscope inserted in an examinee, an analysis processing unit that generates analysis data corresponding to the coordinate values of the plurality of predetermined locations based on the insertion state information, a storing section that stores the analysis data and a display control unit that calculates a display period control value based on latest analysis data and one or a plurality of pieces of past analysis data of the analysis data stored in the storing section and judges whether or not to display insertion assisting information, which is information that can support the insertion operation of the insertion portion based on the display period control value on a display unit.

DETAILED DESCRIPTION OF THE PREFERRED EMBODIMENTS

Hereinafter, embodiments of the present invention will be explained with reference to the accompanying drawings.

First Embodiment

Figure 1:
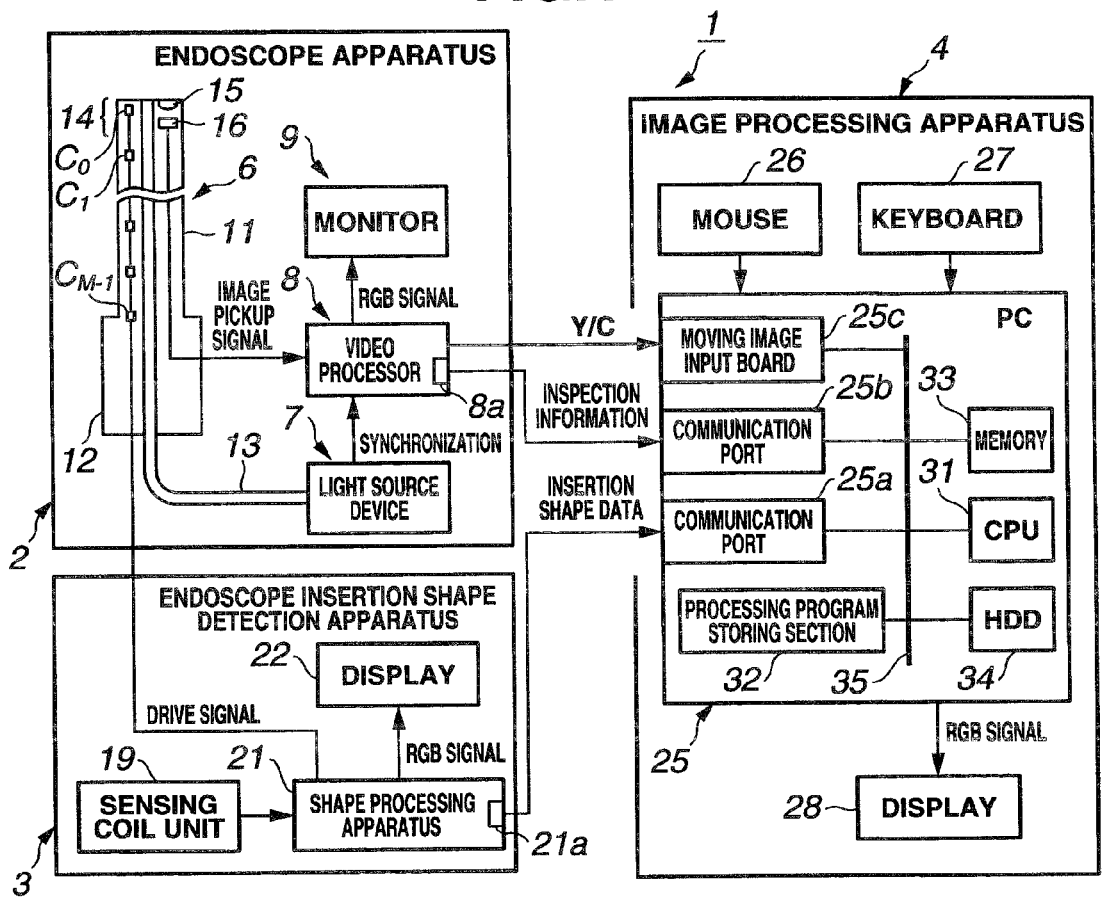
FIG. 1 shows an example of a configuration of main parts of a biological observation system provided with an endoscope insertion shape analysis system according to an embodiment of the present invention.
Figure 2:
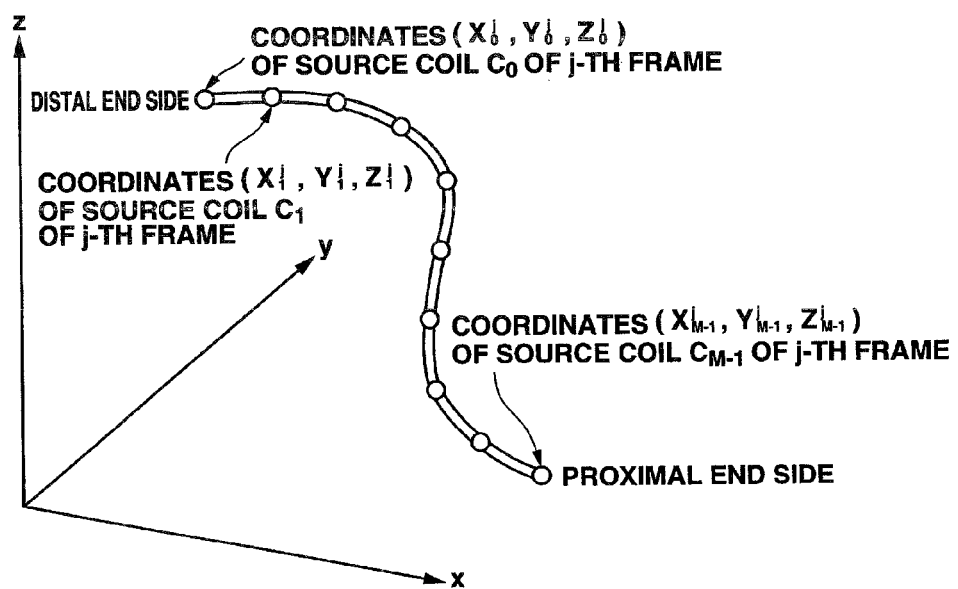
FIG. 2 shows coordinates of a source coil provided for an insertion portion of the endoscope in FIG. 1 detected by the endoscope insertion shape detection apparatus in FIG. 1.
Figure 3A:
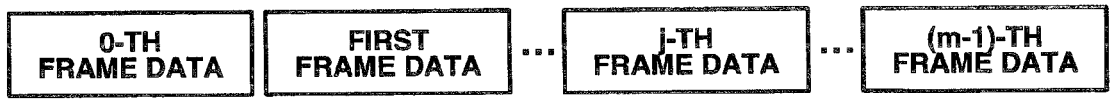
FIG. 3A shows an overview of insertion shape data generated by the endoscope insertion shape detection apparatus in FIG. 1.
Figure 3B:
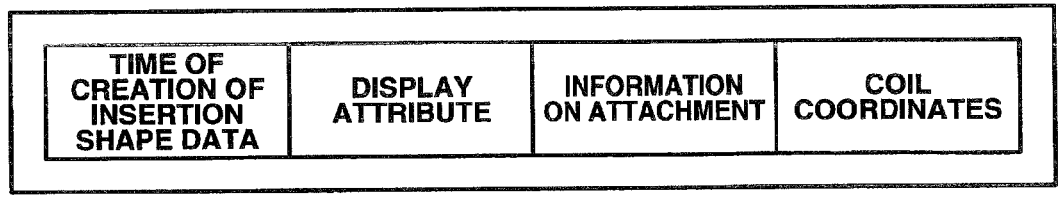
FIG. 3B shows an overview of data and information included in the frame data in FIG. 3A.
Figure 3C:
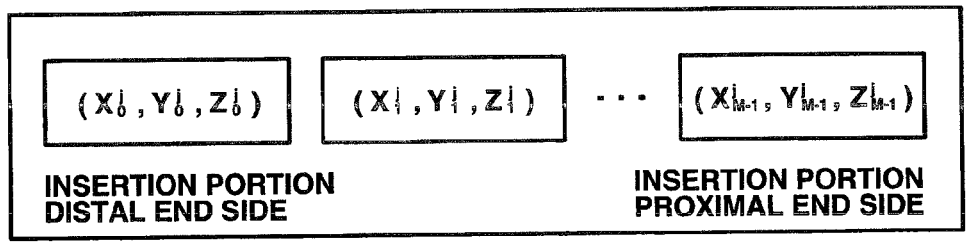
FIG. 3C shows an overview of three-dimensional coordinate data included in the coil coordinate data in FIG. 3B.
Figure 4:
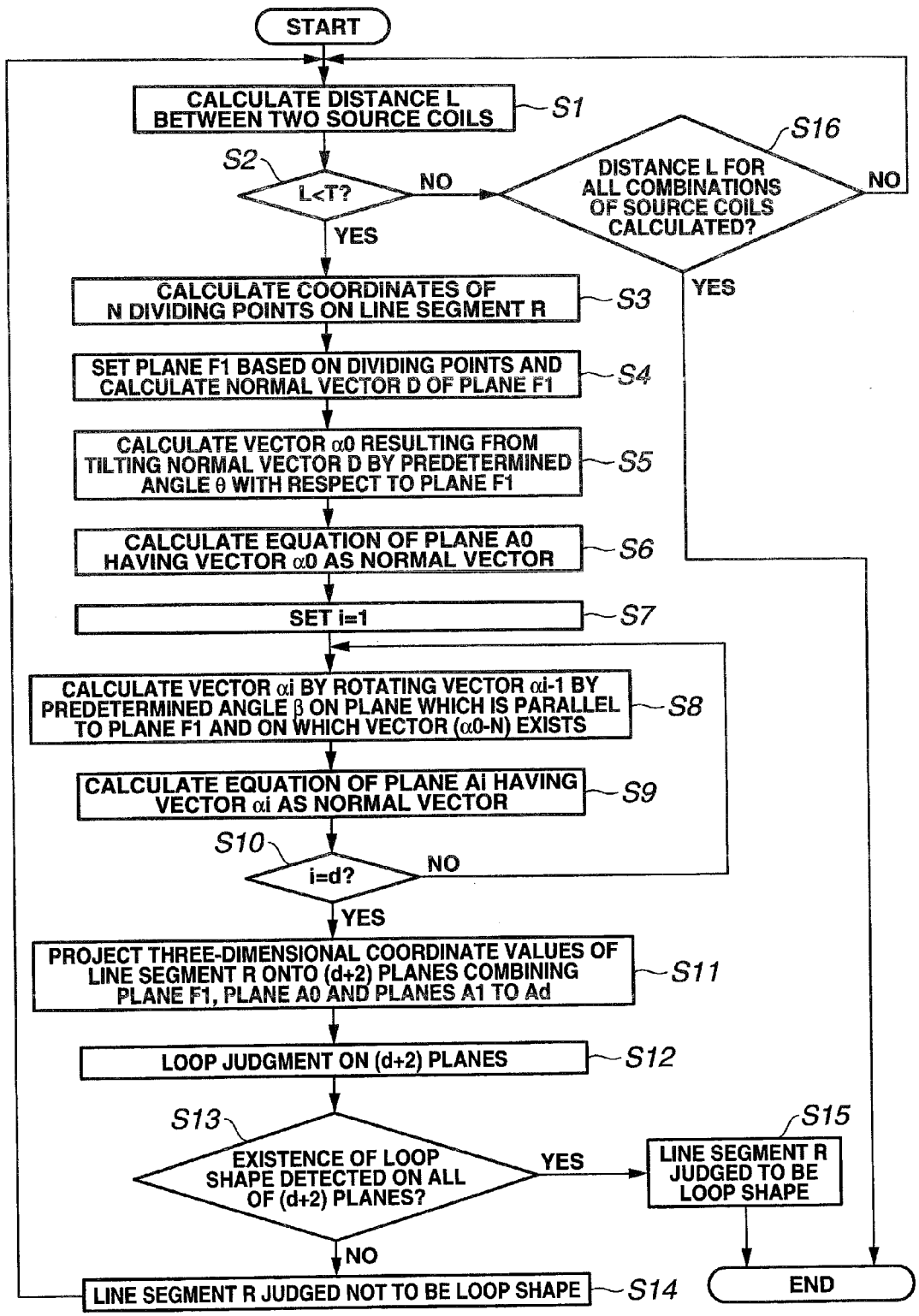
FIG. 4 is a flowchart showing an example of processing performed when judging the presence/absence of a loop shape in a first embodiment of the present invention.
Figure 5:
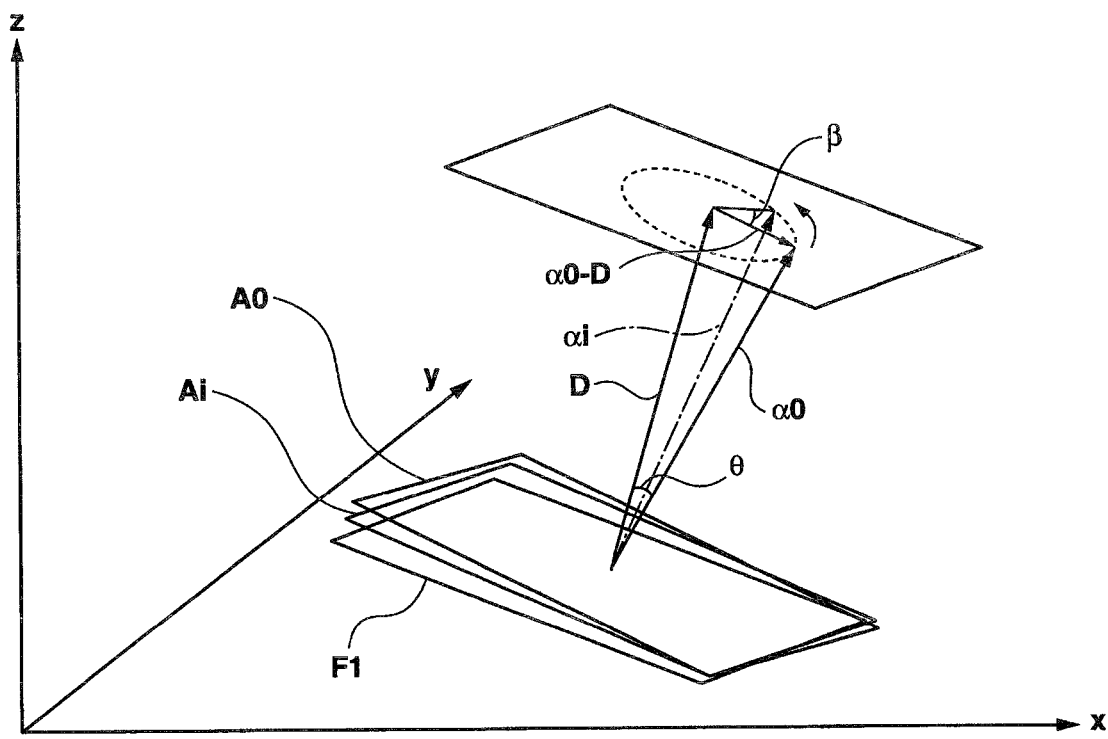
FIG. 5 shows a geometrical overview of processing of the flowchart in FIG. 4.

FIG. 1 to FIG. 5 relate to a first embodiment of the present invention. FIG. 1 shows an example of main parts of a biological observation system according to the embodiment of the present invention. FIG. 2 shows coordinates of a source coil provided for an insertion portion of the endoscope in FIG. 1 detected by the endoscope insertion shape detection apparatus in FIG. 1. FIG. 3A shows an overview of insertion shape data generated by the endoscope insertion shape detection apparatus in FIG. 1. FIG. 3B shows an overview of data and information included in the frame data in FIG. 3A. FIG. 3C shows an overview of three-dimensional coordinate data included in the coil coordinate data in FIG. 3B. FIG. 4 is a flowchart showing an example of processing performed when judging the presence/absence of a loop shape in a first embodiment. FIG. 5 shows a geometrical overview of processing of the flowchart in FIG. 4.

As shown in FIG. 1, the biological observation system 1 is configured by including an endoscope apparatus 2 that can observe the interior of an examinee through an endoscope 6, an endoscope insertion shape detection apparatus 3 that detects an insertion shape of the endoscope 6 inserted in the examinee and outputs the insertion shape as insertion shape data and an image processing apparatus 4 that performs various types of processing according to the insertion shape data outputted from the endoscope insertion shape detection apparatus 3.

The endoscope apparatus 2 can be inserted into the large intestine or the like located inside the examinee and is configured by including the endoscope 6 that picks up an image of an object inside the examinee and outputs the image as an image pickup signal, a light source device 7 that supplies illuminating light for illuminating the object to the endoscope 6, a video processor 8 that performs signal processing on the image pickup signal outputted from the endoscope 6 and outputs the signal as a video signal, and a monitor 9 that displays the image of the object picked up by the endoscope 6 as an endoscope observed image based on the video signal outputted from the video processor 8.

The endoscope 6 includes an elongated insertion portion 11 that can be inserted in the examinee and an operation portion 12 provided at a rear end of the insertion portion 11. Inside the insertion portion 11, a light guide 13 is inserted, one end of which is disposed at a distal end portion 14 of the insertion portion 11 and the other end of which can be connected to the light source device 7. This allows the illuminating light supplied from the light source device 7 to be emitted from an illumination window (not shown) provided at the distal end portion 14 of the insertion portion 11 via the light guide 13.

A bending portion (not shown) configured to be flexible is provided on a rear end side of the distal end portion 14 of the insertion portion 11. The bending portion (not shown) can be bent by operating a bending operation knob (not shown) or the like provided at the operation portion 12.

An objective lens 15 is attached to an observation window (not shown) disposed neighboring the illumination window (not shown) at the distal end portion 14. Furthermore, the image pickup plane of an image pickup device 16 made up of a charge coupled device (abbreviated as "CCD") is disposed at an image forming position of the objective lens 15.

The image pickup device 16 is connected to the video processor 8 via a signal line and photoelectrically converts the image of the object formed by the objective lens 15 to an image pickup signal and outputs the image pickup signal to the video processor 8.

The video processor 8 performs signal processing for generating a video signal based on the image pickup signal outputted from the image pickup device 16. The video processor 8 then outputs, for example, an RGB signal, which is a video signal generated from the signal processing to the monitor 9. An image of the object picked up by the image pickup device 16 is displayed on the display plane of the monitor 9 as an endoscope observed image.

When supplying frame sequential illuminating light made up of R (red), G (green) and B (blue), suppose the light source device 7 outputs a synchronization signal synchronized with the periods at which the respective parts of light are supplied to the video processor 8. In this case, suppose the video processor 8 performs signal processing in synchronization with the synchronization signal outputted from the light source device 7.

The operation portion 12 of the endoscope 6 is provided with a switch (not shown) that can give a release instruction or the like in addition to the aforementioned bending operation knob (not shown).

Furthermore, a plurality of source coils $C_0, C_1, \ldots, C_{M-1}$ (abbreviated as "$C_0$ to $C_{M-1}$") are arranged in the interior of the insertion portion 11 of the endoscope 6 at predetermined intervals in a longitudinal direction. The source coils $C_0$ to $C_{M-1}$ then generate magnetic fields in the periphery according to a drive signal outputted from the endoscope insertion shape detection apparatus 3.

The magnetic fields generated from the source coils $C_0$ to $C_{M-1}$ are detected by a sensing coil unit 19 that incorporates a plurality of sensing coils provided for the endoscope insertion shape detection apparatus 3.

The endoscope insertion shape detection apparatus 3 is configured by including the sensing coil unit 19 that detects magnetic fields generated from the source coils $C_0$ to $C_{M-1}$ provided for the endoscope 6, a shape processing apparatus 21 that estimates a shape (insertion shape) of the insertion portion 11 based on the detected signals of the magnetic fields detected by the sensing coil unit 19 and a display 22 that displays the insertion shape estimated by the shape processing apparatus 21.

The sensing coil unit 19 that forms part of an insertion state acquisition unit is disposed in the periphery or the like of an inspection bed on which a patient lies, detects the magnetic fields from the source coils $C_0$ to $C_{M-1}$ and outputs the detected magnetic fields to the shape processing apparatus 21 as detected signals.

The shape processing apparatus 21 that forms part of an insertion state acquisition unit and has a function of an insertion shape detection unit calculates position coordinate data of the source coils $C_0$ to $C_{M-1}$ based on the detected signals and also estimates the insertion shape of the insertion portion 11 based on the calculated position coordinate data. Furthermore, the shape processing apparatus 21 generates a video signal of the estimated insertion shape of the insertion portion 11 and outputs, for example, an RGB signal which is the video signal generated to the display 22. In this way, an image of the insertion shape of the insertion portion 11 is displayed on a display screen of the display 22. Furthermore, in the middle of an observation being performed by the endoscope 6, the shape processing apparatus 21 consecutively generates three-dimensional coordinate information indicating the insertion shape of the insertion portion 11 and insertion shape data such as shape display attributes and outputs the information and data to the image processing apparatus 4 via a communication port 21a.

Suppose the shape processing apparatus 21 of the present embodiment can output only insertion shape data to the image processing apparatus 4 when, for example, a release switch is operated.

Furthermore, suppose the endoscope insertion shape detection apparatus 3 of the present embodiment can change the shape display attributes such as a rotation angle and scaling factor of the image of the insertion shape generated through shape detection processing by the shape processing apparatus 21 and then displayed on the display 22 by instructing and inputting the shape display attributes from an operation panel (not shown) or the like.

The video processor 8 has the operation panel (not shown) to input inspection information which is information such as a name, birth date, sex, age, patient code and inspection date and time of the patient. The inspection information inputted from the operation panel (not shown) is also transmitted to the image processing apparatus 4 via a communication port 8a.

The image processing apparatus 4 has a personal computer (hereinafter simply referred to as "PC") 25 that carries out analysis processing to generate insertion assisting information that can assist or support the user's operation of inserting the insertion portion 11 based on the insertion shape data outputted from the endoscope insertion shape detection apparatus 3 and the inspection information outputted from the video processor 8, a mouse 26 and a keyboard 27 that can give various instructions and inputs to the PC 25, and a display 28 that can reproduce or display insertion assisting information or the like generated through analysis processing of the PC 25.

The PC 25 includes a communication port 25a that incorporates insertion shape data outputted from the communication port 21a of the shape processing apparatus 21 of the endoscope insertion shape detection apparatus 3, a communication port 25b that incorporates inspection information outputted from the communication port 8a of the video processor 8 of the endoscope apparatus 2, a moving image input board 25c that converts a video signal of a moving image generated by the video processor 8 to predetermined compression image data, a CPU 31 that performs various types of processing and control, a processing program storing section 32 that stores processing programs used for the image processing by the CPU 31, a memory 33 that temporarily stores data or the like processed by the CPU 31, a hard disk (hereinafter simply referred to as "HDD") 34 that stores image data or the like processed by the CPU 31. The respective units of the PC 25 are mutually connected by a bus line 35.

For example, a Y/C signal is inputted to the moving image input board 25c of the image processing apparatus 4 as a video signal of the moving image generated by the video processor 8. The moving image input board 25c then converts the video signal of the moving image to compressed moving image data using a predetermined compression format such as MJPEG format and outputs the compressed moving image data to the HDD 34.

The insertion shape data incorporated by the communication port 25a and the inspection information incorporated by the communication port 25b are outputted to the HDD 34 and can thereby be saved in the PC 25.

Furthermore, suppose the endoscope insertion shape analysis system of the present embodiment is configured by including the sensing coil unit 19, the shape processing apparatus 21 and the CPU 31 as main parts.

Here, the processing that the endoscope insertion shape detection apparatus 3 performs to generate insertion shape data will be explained.

The shape processing apparatus 21 of the endoscope insertion shape detection apparatus 3 generates insertion shape data including three-dimensional coordinates including M source coils $C_0$ to $C_{M-1}$ incorporated in the insertion portion 11 of the endoscope 6 according to the timing at which image pickup signals corresponding to one frame are outputted from the image pickup device 16 of the endoscope 6. Furthermore, the shape processing apparatus 21 outputs the insertion shape data to the image processing apparatus 4, generates an image of the insertion shape of the insertion portion 11 based on the insertion shape data and outputs an image of the insertion shape to the display 22.

Suppose three-dimensional coordinates of an i-th (i=0, 1, . . . , M−1) source coil Ci from the distal end side of the insertion portion 11 in a j-th frame (j=0, 1, 2 . . . ) are expressed as $(X_i^j, Y_i^j, Z_i^j)$ as shown in FIG. 2.

The insertion shape data including data in the coordinate system of the source coils $C_0$ to $C_{M-1}$ detected by the endoscope insertion shape detection apparatus 3 is configured as frame data (that is, 0-th frame data, first frame data, . . . ) related to each frame as shown in FIG. 3A and sequentially transmitted to the image processing apparatus 4. As shown in FIG. 3B, the frame data as the insertion state information is configured by including data such as a time of creation of the insertion shape data, display attribute, information on attachment and three-dimensional coordinate data (coil coordinate data) of the source coils or the like.

Furthermore, as shown in FIG. 3C, the coil coordinate data is data that indicates the three-dimensional coordinates of the source coils $C_0$ to $C_{M-1}$ sequentially arranged from the distal end side of the insertion portion 11 to the proximal end side (operation portion 12 side). Suppose the three-dimensional coordinates of the source coils outside the detection range of the endoscope insertion shape detection apparatus 3, for example, are set as predetermined coordinate values (e.g., (0,0,0)) which makes it obvious that the source coils are outside the detection range.

Next, operations of the biological observation system 1 of the present embodiment will be explained.

When the user inserts the insertion portion 11 of the endoscope 6 from the anus of the examinee into the body cavity, an image of an object located in the body cavity is picked up by the image pickup device 16 provided at the distal end portion 14 of the insertion portion 11. The image of the object picked up by the image pickup device 16 is outputted as an image pickup signal, subjected to signal processing by the video processor 8, converted to a video signal and then outputted to the monitor 9. This causes the image of the object picked up by the image pickup device 16 to be displayed on the monitor 9 as an endoscope observed image.

The endoscope insertion shape detection apparatus 3 detects the magnetic fields emitted from the source coils $C_0$ to $C_{M-1}$ by the sensing coil unit 19 and estimates the insertion shape of the insertion portion 11 based on the detected signals outputted according to the magnetic fields by the shape processing apparatus 21. This causes the insertion shape of the insertion portion 11 estimated by the shape processing apparatus 21 to be displayed on the display 22.

Furthermore, the shape processing apparatus 21 of the endoscope insertion shape detection apparatus 3 sequentially outputs frame data including position information of the respective source coils to the CPU 31 of the PC 25 of the image processing apparatus 4 via the communication port 21a.

The CPU 31 performs processing shown in the flowchart in FIG. 4 as the processing for judging whether or not the insertion portion 11 inserted in the examinee has formed a loop shape based on the insertion shape data outputted from the endoscope insertion shape detection apparatus 3. FIG. 5 shows a geometrical overview of the processing of the flowchart in FIG. 4.

First, the CPU 31 calculates a distance L between any two source coils (step S1 in FIG. 4) based on the data of the three-dimensional coordinates of the source coils $C_0$ to $C_{M-1}$ of the insertion shape data outputted from the endoscope insertion shape detection apparatus 3 and detects whether or not the calculated distance L is less than a threshold T. Upon detecting that the distance L is less than the threshold T (step S2 in FIG. 4), the CPU 31 performs processing in step S3 in FIG. 4, which will be described later. On the other hand, upon detecting that the distance L is equal to or greater than the threshold T (step S2 in FIG. 4), the CPU 31 further detects whether or not the distance L between the two source coils has been calculated for all combinations of the source coils $C_0$ to $C_{M-1}$. The present embodiment assumes that the distance L between two source coils indicates a straight distance from one source coil to the other source coil.

Upon detecting that the distance L between the two source coils has been calculated for all combinations of the source coils $C_0$ to $C_{M-1}$ (step S16 in FIG. 4), the CPU 31 ends a series of processes. On the other hand, upon detecting that there are still combinations of the source coils $C_0$ to $C_{M-1}$ for which distance L between the two source coils has not been calculated (step S16 in FIG. 4), the CPU 31 performs the processing from step S1 in FIG. 4 onward again.

Upon detecting the two source coils whose distance L is less than the threshold T in step S2 in FIG. 4, the CPU 31 divides a line segment R which is a line segment generated based on the insertion shape between the two source coils in the insertion portion 11 inserted in the examinee and thereby calculates coordinate values of N dividing points of the line segment R (step S3 in FIG. 4). The line segment R may also be generated using part of the insertion shape of the insertion portion 11 estimated by the endoscope insertion shape detection apparatus 3 or may be generated by applying the equation of a Catmull-Rom curve to the data of three-dimensional coordinates of the source coils $C_0$ to $C_{M-1}$.

The CPU 31 then sets a plane F1 on which the line segment R is located based on the N dividing points generated in the processing in step S3 in FIG. 4 and calculates a normal vector D of the plane F1 (step S4 in FIG. 4).

To be more specific, the CPU 31 as the coordinate plane setting unit sets the following expression (1) as the equation of the plane F1 by substituting coordinate values (V1x, V1y, V1z), (V2x, V2y, V2z), . . . , (VNx, VNy, VNz) at the N dividing points of the line segment R into the equation of a general plane respectively.

$$(1\ 1\ \ldots\ 1) = (a\ b\ c) \begin{pmatrix} V1x & V2x & \ldots & VNx \\ V1y & V2y & \ldots & VNy \\ V1z & V2z & \ldots & VNz \end{pmatrix} \quad (1)$$

$$A = \begin{pmatrix} V1x & V2x & \ldots & VNx \\ V1y & V2y & \ldots & VNy \\ V1z & V2z & \ldots & VNz \end{pmatrix} \quad (2)$$

Suppose the matrix on the left side of expression (1) is a matrix made up of one row and N columns. Furthermore, a matrix A in expression (2) is the same matrix as the second matrix on the right side of expression (1) and is a matrix made up of three rows and N columns.

The CPU 31 calculates values of a normal vector D (a, b, c) by calculating a pseudo-inverse matrix $A^+$ of the matrix A in expression (2) above and applying LU decomposition in expression (1) above.

Next, the CPU 31 calculates a vector α0 resulting from tilting the normal vector D (a, b, c) by an angle θ (e.g., 10 degrees) with respect to the plane F1 (step S5 in FIG. 4) and calculates a plane A0 whose normal vector is the vector α0 (step S6 in FIG. 4).

Furthermore, the CPU 31 sets variable i (i=1, 2, ..., d) to 1 (step S7 in FIG. 4), then calculates a vector $\alpha i$ resulting from rotating a vector $\alpha i-1$ by an angle $\beta$ (e.g., 45 degrees) on a plane parallel to the plane F1 and on which a vector ($\alpha 0-N$) is located (step S8 in FIG. 4) and calculates a plane Ai whose normal vector is the vector $\alpha i$ (step S9 in FIG. 4).

The CPU 31 as the coordinate plane setting unit repeatedly performs the aforementioned processing in step S8 and step S9 in FIG. 4 until variable i becomes d, that is, until the CPU 31 calculates planes A1 to Ad whose normal vectors are vectors $\alpha 1$ to $\alpha d$ respectively (step S10 in FIG. 4).

The CPU 31 as the insertion shape projecting unit projects the respective three-dimensional coordinate values of the line segment R onto a total of (d+2) planes of the plane F1 calculated by the processing in step S3 and step S4 in FIG. 4, plane A0 calculated by the processing in step S5 and step S6 in FIG. 4 and planes A1 to Ad calculated by repeating the processing from step S7 to step S10 in FIG. 4 (step S11 in FIG. 4).

Then, the CPU 31 as the insertion shape judging unit carries out processing of judging loop shapes on the (d+2) planes based on the respective three-dimensional coordinate values of line segment R projected onto the (d+2) planes (step S12 in FIG. 4). To be more specific, the CPU 31 calculates a power spectrum based on a P-type Fourier descriptor from, for example, the respective three-dimensional coordinate values of the line segment R projected onto the (d+2) planes, compares the calculated power spectrum with one or a plurality of predetermined power spectra corresponding to pattern data (instructor data) of one or a plurality of loop shapes written in the HDD 34 beforehand and judges, when predetermined conditions are met, that the line segment R forms a loop shape. The method of judging whether or not one line segment forms a loop shape using the aforementioned P-type Fourier descriptor and power spectrum is described in Japanese Patent Application Laid-Open Publication No. 2004-358095, and therefore detailed explanations thereof will be omitted here.

The CPU 31 as the insertion shape judging unit judges, when the existence of the loop shape is not detected on any one of the (d+2) planes based on the loop judgment in step S12 in FIG. 4 (step S13 in FIG. 4), that the line segment R does not form any loop shape (step S14 in FIG. 4) and performs processing from step S1 in FIG. 4 onward again in combinations of the other two source coils different from the combinations of the two source coils to be processed so far. Furthermore, when the existence of the loop shape is detected on all the (d+2) planes (step S113 in FIG. 4) based on the loop judgment in step S12 in FIG. 4, the CPU 31 as the insertion shape judging unit judges that the line segment R forms a loop shape (step S15 in FIG. 4) and ends a series of processes.

As described above, the biological observation system 1 provided with the endoscope insertion shape analysis system of the present embodiment has a configuration capable of judging whether or not the insertion shape forms a loop shape while setting the coordinate plane onto which the insertion shape of the insertion portion 11 is projected for a plurality of coordinate planes corresponding to the insertion shape. As a result, the biological observation system 1 provided with the endoscope insertion shape analysis system of the present embodiment can accurately detect the loop shape formed by the insertion portion 11 of the endoscope 6.

Second Embodiment

Figure 6:
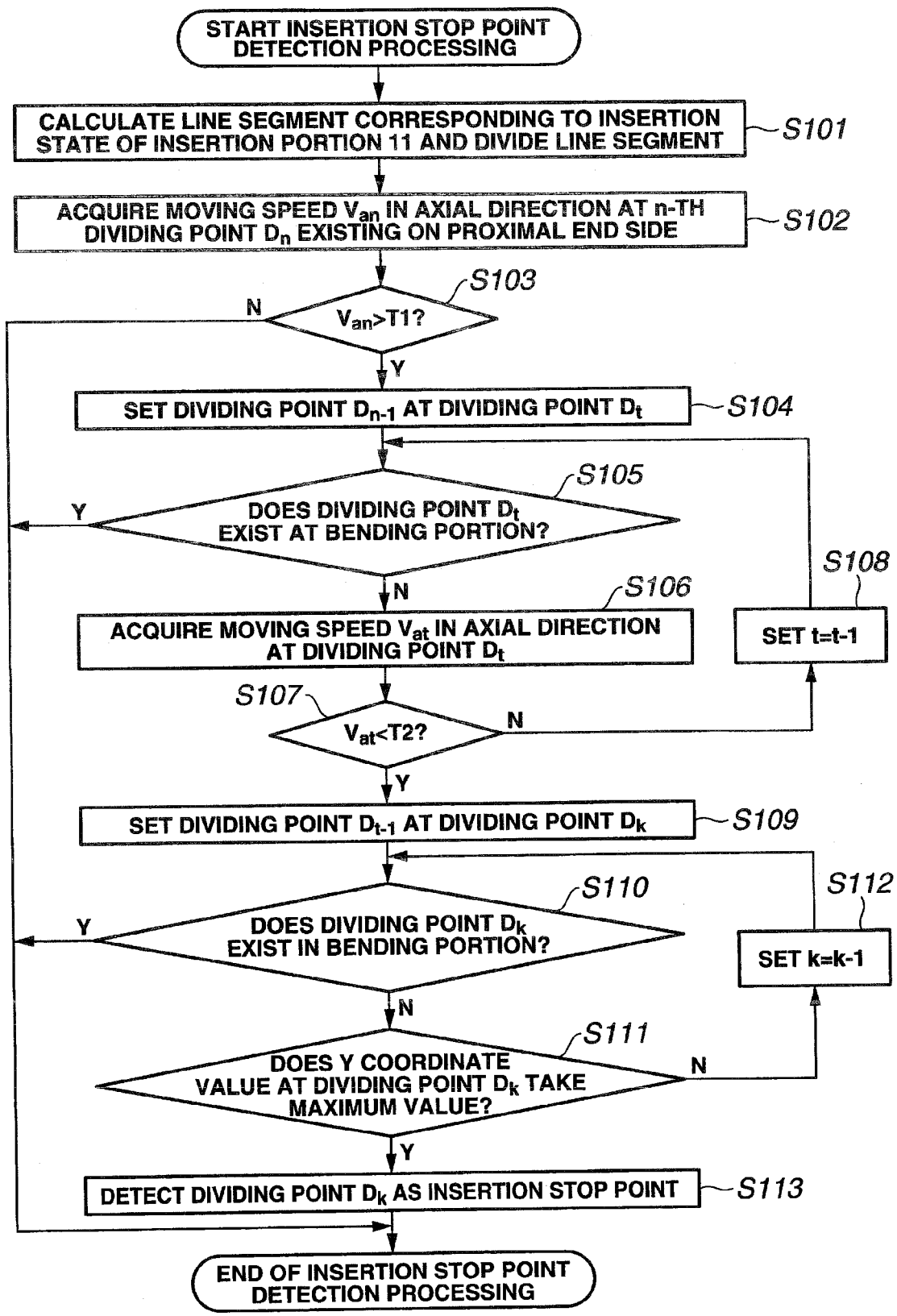
FIG. 6 is a flowchart showing an example of processing performed when detecting an insertion stop point in a second embodiment of the present invention.
Figure 7:
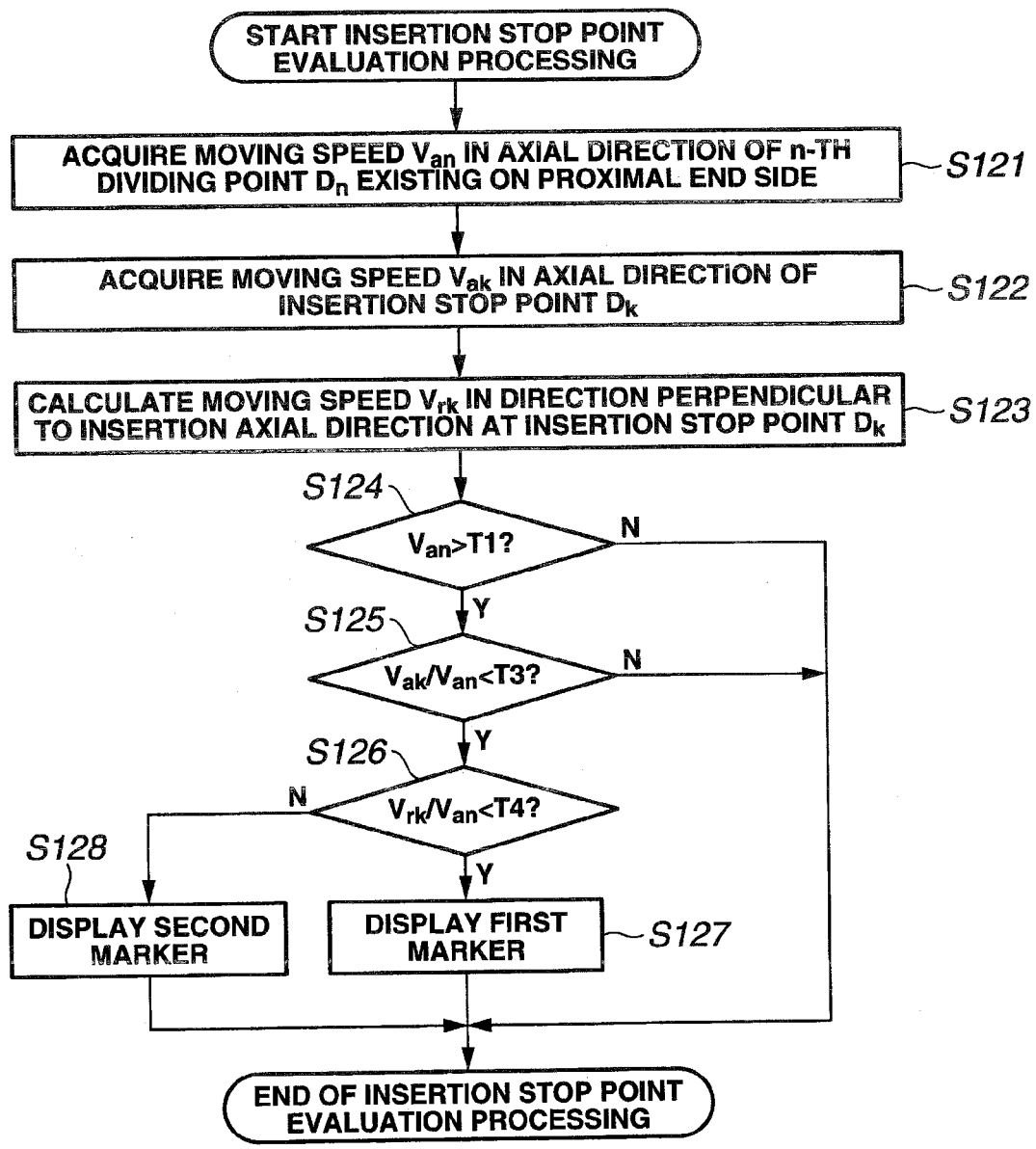
FIG. 7 is a flowchart showing an example of processing performed when evaluating the insertion stop point detected by a series of processes in FIG. 6 according to the second embodiment of the present invention.
Figure 8:
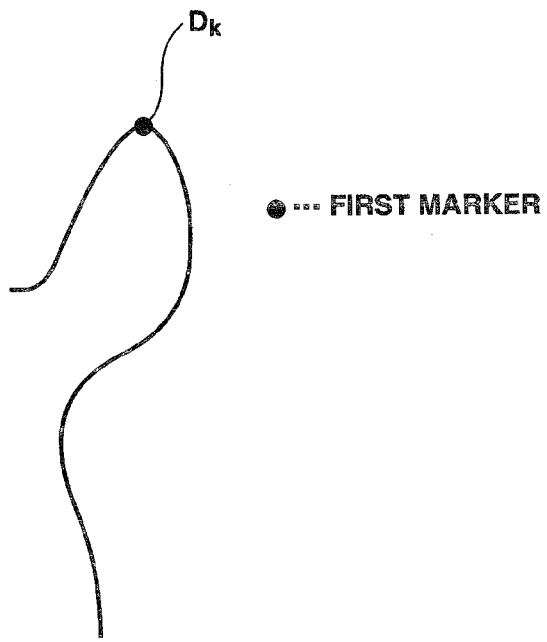
FIG. 8 shows an example of a first marker displayed on the display according to the processing result of the series of processes in FIG. 7.
Figure 9:
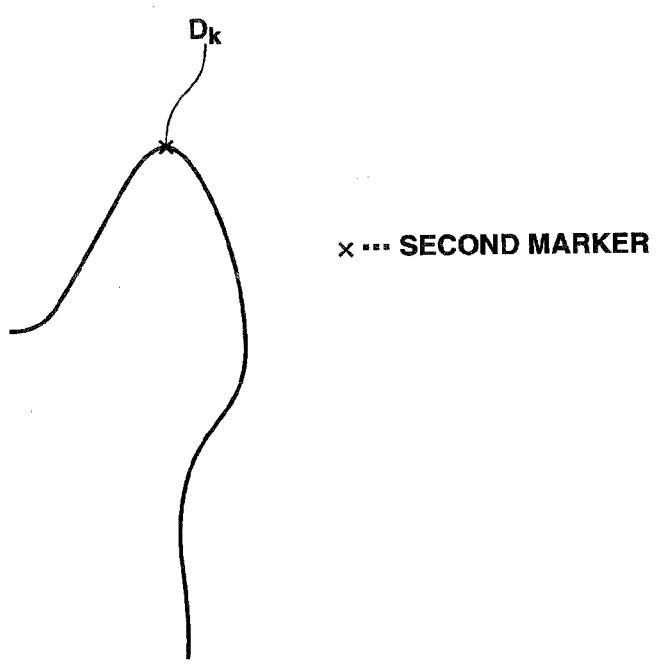
FIG. 9 shows an example of a second marker displayed on the display according to the processing result of the series of processes in FIG. 7.
Figure 10:
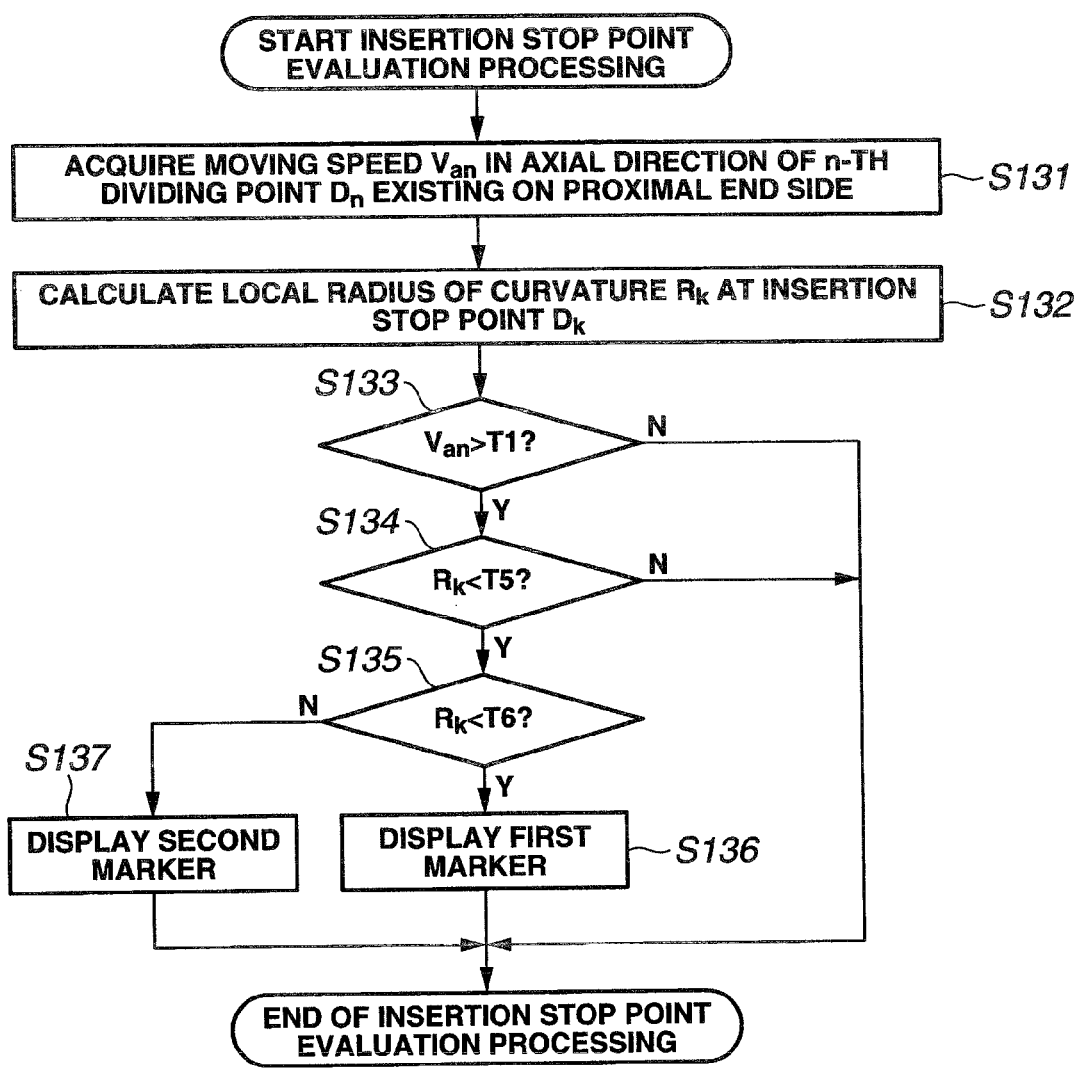
FIG. 10 is a flowchart showing an example of the processing performed when evaluating the insertion stop point detected by a series of processes in FIG. 6 according to the second embodiment of the present invention, which is different from FIG. 7.

FIG. 6 to FIG. 10 relate to a second embodiment of the present invention. FIG. 6 is a flowchart showing an example of processing performed when detecting an insertion stop point in the second embodiment of the present invention. Furthermore, FIG. 7 is a flowchart showing an example of processing performed when evaluating the insertion stop point detected by a series of processes in FIG. 6 according to the second embodiment of the present invention. FIG. 8 shows an example of a first marker displayed on the display according to the processing result of a series of processes in FIG. 7. FIG. 9 shows an example of a second marker displayed on the display according to the processing result of a series of processes in FIG. 7. FIG. 10 is a flowchart showing an example of the processing performed when evaluating the insertion stop point detected by a series of processes in FIG. 6 according to the second embodiment of the present invention, which is different from FIG. 7.

The biological observation system of the second embodiment has a configuration substantially the same as the biological observation system 1 explained in the first embodiment. Therefore, in the present embodiment, suppose explanations of parts having the same configurations or operations as those in the biological observation system 1 of the first embodiment will be omitted and explanations will be focused on those having configurations or operations different from those in the biological observation system 1 of the first embodiment. Furthermore, suppose the endoscope insertion shape analysis system of the present embodiment is configured by including the shape processing apparatus 21 and the CPU 31 as main parts.

Next, operations of the biological observation system 1 in the present embodiment will be explained.

When the user inserts the insertion portion 11 of the endoscope 6 from the anus of the examinee into the body cavity, an image of an object located in the body cavity is picked up by the image pickup device 16 provided at the distal end portion 14 of the insertion portion 11. The image of the object picked up by the image pickup device 16 is outputted as an image pickup signal, subjected to signal processing by the video processor 8, converted to a video signal and then outputted to the monitor 9. This causes the image of the object picked up by the image pickup device 16 to be displayed on the monitor 9 as an endoscope observed image.

The endoscope insertion shape detection apparatus 3 detects the magnetic fields emitted from the source coils $C_0$ to $C_{M-1}$ by the sensing coil unit 19 and estimates the insertion shape of the insertion portion 11 based on the detected signals outputted according to the magnetic fields by the shape processing apparatus 21. This causes the insertion shape of the insertion portion 11 estimated by the shape processing apparatus 21 to be displayed on the display 22.

Furthermore, the shape processing apparatus 21 of the endoscope insertion shape detection apparatus 3 sequentially outputs frame data including position information of the respective source coils to the CPU 31 of the PC 25 of the image processing apparatus 4 via the communication port 21a.

Based on frame data sequentially outputted from the endoscope insertion shape detection apparatus 3, the CPU 31 performs insertion stop point detection processing shown in the flowchart in FIG. 6 as the processing to detect insertion stop points, which are locations where there are factors to stop the user's operation of inserting the insertion portion 11, of the insertion portion 11 inserted in the examinee.

First, the CPU 31 as an insertion shape dividing unit applies, for example, the equation of a Catmull-Rom curve to coil coordinate data of the frame data sequentially outputted from the endoscope insertion shape detection apparatus 3, thereby calculates a line segment corresponding to insertion states of the insertion portion 11 formed by the respective source coils from the source coil (source coil $C_0$) disposed on the most distal end side of the insertion portion 11 inserted in the examinee to the source coil disposed on the most proximal end side of the insertion portion 11 inserted in the examinee and divides the line segment (step S101 in FIG. 6). Suppose the CPU 31 divides the line segment corresponding to the insertion state of the insertion portion 11 in the aforementioned processing in step S101 in FIG. 6 by, for example, n dividing points $D_1$ to $D_n$. Furthermore, in the present embodiment, suppose the dividing points are set as $D_1, D_2, \ldots, D_{n-1}$, $D_n$ from the distal end side to the proximal end side. Furthermore, suppose the respective dividing points are divided and set so as to be uniformly spaced such that the distance between neighboring dividing points becomes a predetermined value d.

Furthermore, the CPU 31 calculates moving speeds $V_1$ to $V_n$ at n dividing points $D_1$ to $D_n$ from the difference between dividing point coordinate values obtained from past frame data and dividing point coordinate values obtained from the current frame data. Furthermore, the CPU 31 calculates the insertion axial direction at n dividing points $D_1$ to $D_n$ from a first order differential value of the Catmull-Rom curve and also calculates moving speeds $V_{a1}$ to $V_{an}$ in the insertion axial direction at n dividing points $D_1$ to $D_n$ by projecting the moving speeds $V_1$ to $V_n$ at n dividing points $D_1$ to $D_n$ in the insertion axial direction.

Next, the CPU 31 acquires the moving speed $V_{an}$ in the insertion axial direction at the n-th dividing point $D_n$ existing on the proximal end side of the insertion portion 11 inserted in the examinee out of the dividing points $D_1$ to $D_n$ by carrying out the aforementioned calculation (step S102 in FIG. 6), and then further detects whether or not the moving speed $V_{an}$ is greater than a threshold T1 (T1>0). Upon detecting that the moving speed $V_{an}$ is greater than the threshold T1 (step S103 in FIG. 6), the CPU 31 judges that insertion operation has been performed on the insertion portion 11 and continues to perform processing in step S104 in FIG. 6, which will be described later. Furthermore, upon detecting that the moving speed $V_{an}$ is equal to or less than the threshold T1 (step S103 in FIG. 6), the CPU 31 judges that no insertion operation has been performed on the insertion portion 11 and ends the insertion stop point detection processing shown in FIG. 6.

In the present embodiment, suppose the moving speed $V_{an}$ in the insertion axial direction at the n-th dividing point $D_n$ is constant irrespective of time.

After detecting in the processing in step S103 in FIG. 6 that the moving speed $V_{an}$ is greater than the threshold T1, the CPU 31 sets the dividing point $D_{n-1}$ neighboring the distal end portion 14 side from the dividing point $D_n$ as a dividing point $D_t$ (step S104 in FIG. 6).

Furthermore, the CPU 31 reads type information of the endoscope 6 stored in at least one of, for example, the video processor 8, memory 33 and HDD 34 and detects whether or not the dividing point $D_t$ set in the processing in step S104 in FIG. 6 exists in the bending portion (not shown) of the insertion portion 11 based on the type information. Upon detecting that the dividing point $D_t$ exists in the bending portion (not shown) of the insertion portion 11 (step S105 in FIG. 6), the CPU 31 then judges that the dividing point $D_t$ is in a position that can be bent by the user's operation and ends the insertion stop point detection processing shown in FIG. 6. Furthermore, upon detecting that the dividing point $D_t$ does not exist in the bending portion (not shown) of the insertion portion 11 (step S105 in FIG. 6), the CPU 31 continues to perform processing in step S106 in FIG. 6.

Upon detecting in the processing in step S105 in FIG. 6 that the dividing point $D_t$ does not exist in the bending portion (not shown) of the insertion portion 11, the CPU 31 then further acquires a moving speed $V_{at}$ in the insertion axial direction at the dividing point $D_t$ (step S106 in FIG. 6) and detects whether or not the moving speed $V_{at}$ is less than the threshold T2. Upon detecting that the moving speed $V_{at}$ is less than the threshold T2 (step S107 in FIG. 6), the CPU 31 judges that there can be a factor to stop the user's operation of inserting the insertion portion 11 at the dividing point $D_t$ and continues to perform processing in step S109 in FIG. 6, which will be described later. Furthermore, upon detecting that the moving speed $V_{at}$ is equal to or greater than the threshold T2 (step S107 in FIG. 6), the CPU 31 sets a dividing point $D_{t-1}$ neighboring on the distal end portion 14 side from the dividing point $D_t$ (step S108 in FIG. 6) and performs processing on the dividing point $D_{t-1}$ in step S105 to step S107 in FIG. 6 again.

After detecting in the processing in step S107 in FIG. 6 that the moving speed $V_{at}$ is less than the threshold T2, the CPU 31 sets the dividing point $D_{t-1}$ neighboring on the distal end portion 14 from the dividing point $D_t$ as a dividing point $D_k$ (step S109 in FIG. 6).

Furthermore, based on the type information of the aforementioned endoscope 6, the CPU 31 detects whether or not the dividing point $D_k$ set in the processing in step S109 in FIG. 6 exists at the bending portion (not shown) of the insertion portion 11. Upon detecting that the dividing point $D_k$ exists at the bending portion (not shown) of the insertion portion 11 (step S110 in FIG. 6), the CPU 31 judges that the dividing point $D_k$ is at a position that can be bent by the user's operation and ends the insertion stop point detection processing shown in FIG. 6. Furthermore, upon detecting that the dividing point $D_k$ does not exist at the bending portion (not shown) of the insertion portion 11 (step S110 in FIG. 6), the CPU 31 continues to perform the processing in step S111 in FIG. 6.

Upon detecting that the dividing point $D_k$ does not exist at the bending portion (not shown) of the insertion portion 11 (step S110 in FIG. 6), the CPU 31 as the insertion stop point estimation unit then further detects whether or not the y coordinate of the dividing point $D_k$ takes a maximum value (step S111 in FIG. 6). Suppose the y-axis in the present embodiment is set as a coordinate axis from the front side in the body cavity (e.g., anus side) to the back side (e.g., stomach side).

To be more specific, the CPU 31 compares y coordinate values of five dividing points located in the vicinity of the dividing point $D_k$, that is, dividing points $D_{k-2}, D_{k-1}, D_k, D_{k+1}$ and $D_{k+2}$ and judges, when the y coordinate value of the dividing point $D_k$ is detected to be a maximum value, that the y coordinate of the dividing point $D_k$ takes a maximum value.

Upon judging that the y coordinate of the dividing point $D_k$ takes a maximum value (step S111 in FIG. 6), the CPU 31 judges that a factor to stop the user's operation of inserting the insertion portion 11 exists at the dividing point $D_k$, detects the dividing point $D_k$ as a insertion stop point (step S113 in FIG. 6), and then ends the insertion stop point detection processing shown in FIG. 6. Furthermore, upon judging that the y coordinate of the dividing point $D_k$ does not take a maximum value (step S111 in FIG. 6), the CPU 31 sets the dividing point $D_{k-1}$ neighboring on the distal end portion 14 from the dividing point $D_k$ (step S112 in FIG. 6) and performs processing in step S110 and step S111 in FIG. 6 on the dividing point $D_{k-1}$ again.

After that, the CPU 31 performs insertion stop point evaluation processing shown in the flowchart in FIG. 7 as the processing for evaluating the insertion stop point $D_k$ detected in the insertion stop point detection processing in FIG. 6 based on other frame data that exists chronologically after (e.g., one to several frames later) the frame data used in the insertion stop point detection processing in order in FIG. 6.

Based on the other frame data, the CPU 31 acquires a moving speed $V_{an}$ in the insertion axial direction at the n-th dividing point $D_n$ that exists at the proximal end side of the insertion portion 11 inserted in the examinee (step S121 in FIG. 7) and also acquires a moving speed $V_{ak}$ in the insertion axial direction at the insertion stop point $D_k$ (step S122 in FIG. 7).

Furthermore, the CPU 31 acquires a moving speed $V_k$ at the insertion stop point $D_k$ based on the other frame data and calculates a moving speed $V_{rk}$ in a direction perpendicular to the insertion axial direction at the insertion stop point $D_k$ using following expression (3) (step S123 in FIG. 7).

$$V_{rk}=\sqrt{V_k^2-V_{ak}^2} \quad (3)$$

The CPU 31 then detects whether or not the moving speed $V_{an}$ is greater than the threshold T1. Upon detecting that the moving speed $V_{an}$ is greater than the threshold T1 (step S124 in FIG. 7), the CPU 31 judges that insertion operation has been performed on the insertion portion 11 and continues to perform processing in step S125 in FIG. 7, which will be described later. Furthermore, upon detecting that the moving speed $V_{an}$ is equal to or less than the threshold T1 (step S124 in FIG. 7), the CPU 31 judges that either the operation on the insertion portion 11 has not been performed or retracting operation on the insertion portion 11 has been performed, and ends the series of processes in FIG. 7.

Furthermore, the CPU 31 as the insertion stop point estimation unit detects whether or not the ratio of the moving speed $V_{ak}$ to the moving speed $V_{an}$, that is, the value of $V_{ak}/V_{an}$, is less than a threshold T3. Upon detecting that the value of $V_{ak}/V_{an}$, which is a value indicating the transmission rate of the moving speed $V_{an}$ when the insertion portion 11 is inserted is less than the threshold T3 (step S125 in FIG. 7), the CPU 31 continues to perform the processing in step S126 in FIG. 7, which will be described later for evaluating the insertion stop point $D_k$. Furthermore, upon detecting that the value of $V_{ak}/V_{an}$ is equal to or greater than the threshold T3 (step S125 in FIG. 7), the CPU 31 judges that the stretching of the large intestine at the insertion stop point $D_k$ has been relieved and ends the series of processes in FIG. 7.

The CPU 31 detects whether or not the ratio of the moving speed $V_{rk}$ to the moving speed $V_{an}$, that is, the value of $V_{rk}/V_{an}$, is less than the threshold T4. Upon detecting that the value of $V_{rk}/V_{an}$ is less than the threshold T4 (step S126 in FIG. 7), the CPU 31 as the notifying section judges that the large intestine has stretched at the insertion stop point $D_k$, uses the first marker as notifying information indicating the position of the insertion stop point $D_k$ as shown in FIG. 8, for example, performs control so as to display the first marker on the display 28 superimposed on the insertion shape of the insertion portion 11 (step S127 in FIG. 7) and then ends the series of processes in FIG. 7. Furthermore, upon detecting that the value of $V_{rk}/V_{an}$ is equal to or greater than the threshold T4 (step S126 in FIG. 7), the CPU 31 as the notifying section judges that the large intestine is in a condition immediately before stretching at the insertion stop point $D_k$, uses a second marker as notifying information indicating the position of the insertion stop point $D_k$ as shown in FIG. 9, for example, performs control so as to display the second marker on the display 28 superimposed on the insertion shape of the insertion portion 11 (step S128 in FIG. 7) and ends the series of processes in FIG. 7.

Upon judging that the processing in step S103 in FIG. 6, step S124 in FIG. 7 and step S125 in FIG. 7 is any one of a condition in which the operation of the insertion portion 11 has not been performed, a condition in which retracting operation on the insertion portion 11 has been performed and a condition in which the stretching of the large intestine at the insertion stop point $D_k$ has been relieved, suppose the CPU 31 performs processing of hiding the respective markers displayed on the display 28 together.

Furthermore, to indicate that a large load is placed on the patient due to the stretching of the large intestine, as shown in FIG. 8 and FIG. 9, suppose the CPU 31 causes the display 28 to display the shape and (or) size of the first marker indicating the position where the large intestine is stretched due to the insertion portion 11 more prominently than the form and (or) size of the second marker indicating the position immediately before the large intestine is stretched due to the insertion portion 11.

Furthermore, the insertion stop point detection processing shown in FIG. 6 and the insertion stop point evaluation processing shown in FIG. 7 of the present embodiment are not performed exclusively in this order but may be performed in the reverse order.

As described above, the biological observation system 1 provided with the endoscope insertion shape analysis system of the present embodiment can detect positions where the large intestine is stretched, indicate the positions to the user by carrying out the processing shown in FIG. 6 and FIG. 7, and as a result, smoothly perform insertion operation of the insertion portion 11 of the endoscope 6 compared to the prior arts.

The CPU 31 is not limited to detecting positions where the large intestine is stretched due to the insertion portion 11 based on the moving speed $V_{rk}$ in a direction perpendicular to the insertion axial direction at the insertion stop point $D_k$ and may also detect positions where the large intestine is stretched due to the insertion portion 11 based on the local radius of curvature at the insertion stop point $D_k$. In such a case, the CPU 31 performs the insertion stop point evaluation processing shown in the flowchart in FIG. 10 as the processing to evaluate the insertion stop point $D_k$ detected through the insertion stop point detection processing in FIG. 6 (instead of insertion stop point evaluation processing in FIG. 7) based on the other frame data existing chronologically later (e.g., one or several frames later) than the frame data used for the insertion stop point detection processing in FIG. 6.

Here, details of the insertion stop point evaluation processing in FIG. 10 will be explained.

The CPU 31 acquires the moving speed $V_{an}$ in the insertion axial direction of the n-th dividing point $D_n$ existing on the proximal end side of the insertion portion 11 inserted in the examinee based on the other frame data (step S131 in FIG. 10) and calculates a local radius of curvature $R_k$ (step S132 in FIG. 10) at the insertion stop point $D_k$. The local radius of curvature $R_k$ at the insertion stop point $D_k$ can be calculated using, for example, a first order differential value and a second order differential value of the equation of a Catmull-Rom curve.

The CPU 31 then detects whether or not the moving speed $V_{an}$ is greater than the threshold T1. Upon detecting that the moving speed $V_{an}$ is greater than the threshold T1 (step S133 in FIG. 10), the CPU 31 judges that insertion operation on the insertion portion 11 has been performed and continues to perform processing in step S134 in FIG. 10, which will be described later. Furthermore, upon detecting that the moving speed $V_{an}$ is equal to or less than the threshold T1 (step S133 in FIG. 10), the CPU 31 judges any one of conditions that the operation on the insertion portion 11 has not been performed and that retracting operation on the insertion portion 11 has been performed, and ends the series of processes in FIG. 10.

Furthermore, the CPU 31 detects whether or not the local radius of curvature $R_k$ at the insertion stop point $D_k$ is less than a threshold T5. Upon detecting that the local radius of curvature $R_k$ at the insertion stop point $D_k$ is less than the threshold T5 (step S134 in FIG. 10), the CPU 31 continues to perform the processing in step S135 in FIG. 10, which will be described later. On the other hand, upon detecting that the local radius of curvature $R_k$ at the insertion stop point $D_k$ is equal to or greater than the threshold T5 (step S134 in FIG. 10), the CPU 31 judges that the stretching of the large intestine at the insertion stop point $D_k$ has been relieved and ends the series of processes in FIG. 10.

The CPU 31 as the notifying section then detects whether or not the local radius of curvature $R_k$ at the insertion stop point $D_k$ is less than a threshold T6 (T6<T5). Upon detecting that the local radius of curvature $R_k$ at the insertion stop point $D_k$ is less than the threshold T6 (step S135 in FIG. 10), the CPU 31 judges that the large intestine is stretched at the insertion stop point $D_k$, performs control so as to cause the display 28 to display the first marker as notifying information indicating the position of the insertion stop point $D_k$(step S136 in FIG. 10) and then ends the series of processes in FIG. 10. Furthermore, upon detecting that the local radius of curvature $R_k$ at the insertion stop point $D_k$ is equal to or greater than the threshold T6 (step S135 in FIG. 10), the CPU 31 as the notifying section judges that the large intestine is in a condition immediately before stretching at the insertion stop point $D_k$, performs control so as to cause the display 28 to display the second marker as notifying information indicating the position of the insertion stop point $D_k$(step S1037 in FIG. 10) and ends the series of processes in FIG. 10.

Upon judging that the processing in step S133 in FIG. 10 and step S134 in FIG. 10 is any one of conditions that the operation on the insertion portion 11 has not been performed, that retracting operation on the insertion portion 11 has been performed and that the stretching of the large intestine at the insertion stop point $D_k$ has been relieved, suppose the CPU 31 performs processing of hiding the markers displayed on the display 28 together.

Furthermore, to indicate that a large load is placed on the patient due to the stretching of the large intestine, as shown in FIG. 8, suppose the CPU 31 causes the display 28 to display the form and (or) size of the first marker indicating positions where the large intestine is stretched due to the insertion portion 11 more prominently than the form and (or) size of the second marker indicating the position where the large intestine in a condition immediately before stretching due to the insertion portion 11.

Furthermore, the insertion stop point detection processing shown in FIG. 6 and the insertion stop point evaluation processing shown in FIG. 10 of the present embodiment are not performed exclusively in this order but may be performed in the reverse order.

As described above, the biological observation system 1 provided with the endoscope insertion shape analysis system of the present embodiment can detect positions where the large intestine is stretched, indicate the positions to the user by carrying out the processing shown in FIG. 6 and FIG. 10, and as a result, smoothly perform insertion operation of the insertion portion 11 of the endoscope 6 compared to the prior arts.

The aforementioned first marker and second marker are not limited to graphic markers, but may be a character string or graph or the like that can notify the user of stretching of the large intestine. Moreover, the aforementioned first marker and second marker may also be configured to gradually change a display condition thereof as the stretching condition of the large intestine changes.

Furthermore, the CPU 31 of the present embodiment is not limited to the one that performs only one of the insertion stop point evaluation processes shown in FIG. 7 and FIG. 10, but may also simultaneously perform both insertion stop point evaluation processes through parallel processing and evaluate positions where the large intestine is stretched based on the result of the parallel processing to improve the detection accuracy of stretching of the large intestine.

Third Embodiment

Figure 11:
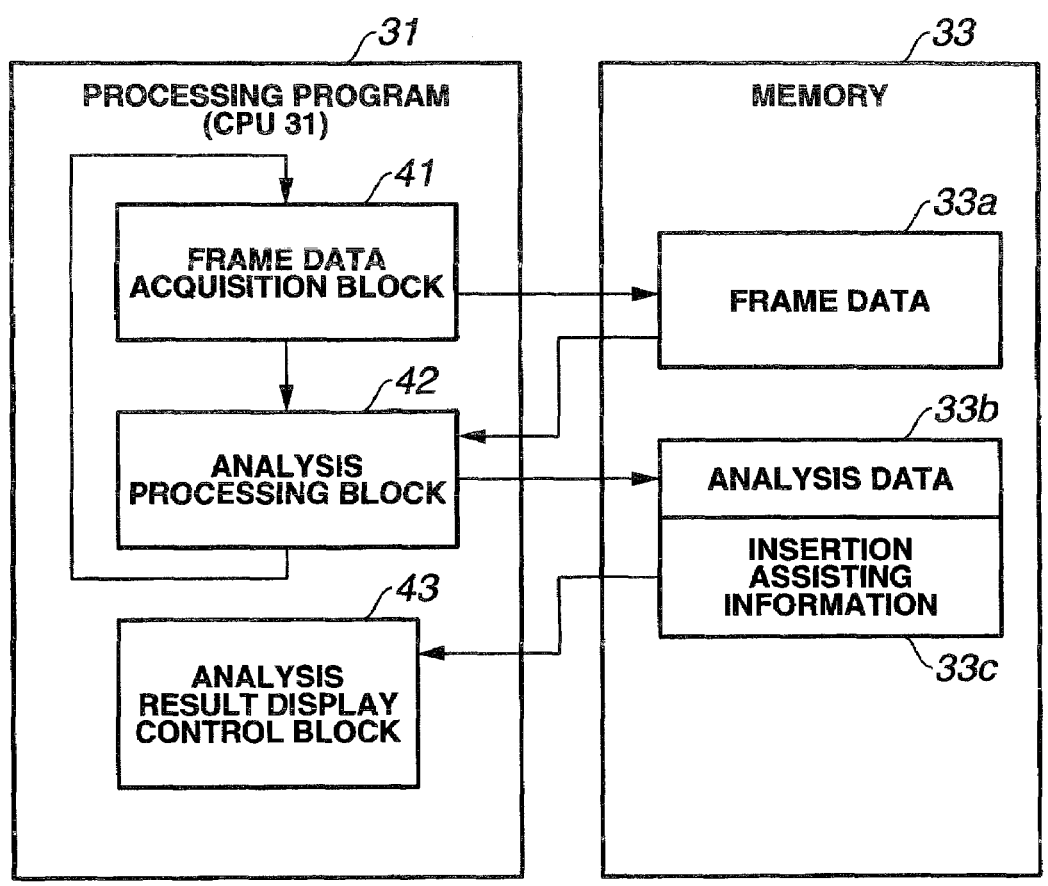
FIG. 11 shows a configuration of function blocks realized by the image processing apparatus in FIG. 1.
Figure 12:
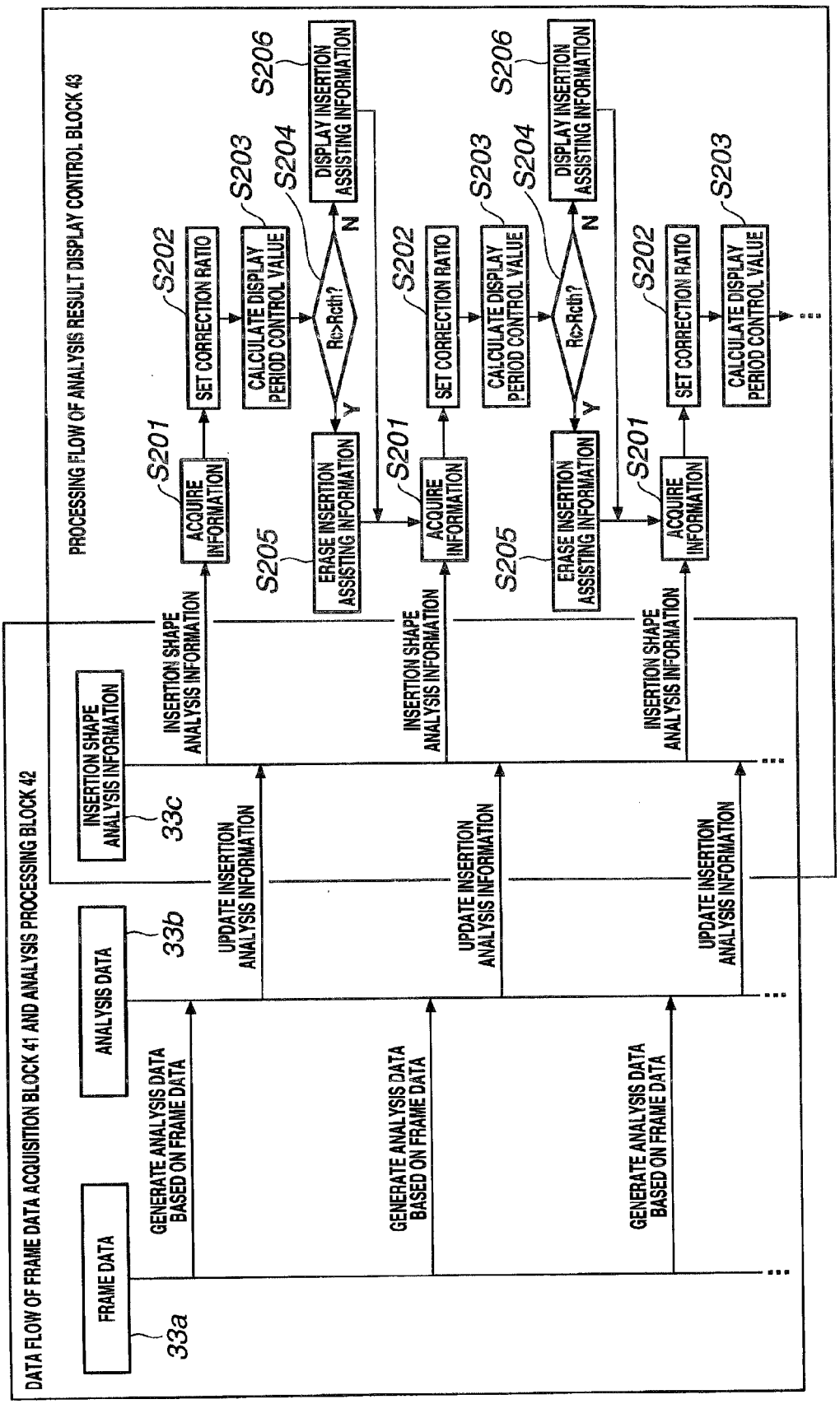
FIG. 12 illustrates a flow of processing performed by the blocks having the configuration shown in FIG. 11 according to a third embodiment of the present invention.

FIG. 11 and FIG. 12 relate to a third embodiment of the present invention. FIG. 11 shows a configuration of function blocks realized by the image processing apparatus in FIG. 1 and FIG. 12 illustrates a flow of processing performed by the respective blocks having the configuration shown in FIG. 11 in the third embodiment of the present invention.

The biological observation system according to the third embodiment has a configuration substantially the same as that of the biological observation system 1 explained in the first embodiment and second embodiment. Therefore, in the present embodiment explanations of the parts having the same configurations or operations as those of the biological observation system 1 of the first embodiment and second embodiment will be omitted and explanations will be focused only on parts having configurations or operations different from those of the biological observation system 1 of the first embodiment and second embodiment. Furthermore, suppose the insertion state acquisition unit in the present embodiment and a fourth embodiment, which will be described later, are configured by including the sensing coil unit 19 and the shape processing apparatus 21.

The CPU 31 of the image processing apparatus 4 according to the present embodiment and the fourth embodiment, which will be described later, performs processing based on a processing program stored in the processing program storing section 32 accompanying an observation by the endoscope apparatus 2.

As shown in FIG. 11, the processing program executed by the CPU 31 is configured by including a frame data acquisition block 41 that acquires frame data and stores the frame data in the memory 33, an analysis processing block 42 that performs analysis processing on the frame data stored in the memory 33 as the storing section and stores analysis data 33b in the memory 33, and an analysis result display control block 43 that displays the analysis result and controls the display (or display characteristic) of the insertion assisting information according to insertion shape analysis information 33c made up of a plurality of pieces of analysis data 33b.

Furthermore, as shown in FIG. 11, the frame data acquisition block 41 and analysis processing block 42 repeatedly perform processing in the form of a loop.

As shown in FIG. 11, the frame data acquisition block 41 stores the frame data transmitted from the endoscope insertion shape detection apparatus 3 in the memory 33 and also in the HDD 34 (shown in FIG. 1).

The analysis processing block 42 as the analysis processing unit calculates data to examine response operation conditions (for insertion operation) of the insertion portion 11 such as the orientation of the insertion portion 11 at each source coil position, amount of movement of the source coil one frame ahead or the like using frame data 33a of the memory 33. The analysis processing block 42 sequentially stores the calculated data in the memory 33 as the analysis data 33b.

On the other hand, the analysis result display control block 43 is a processing block repeatedly performed at predetermined periods of time, which is independent of the aforementioned loop processing of the frame data acquisition block 41 and analysis processing block 42.

The analysis result display control block 43 as the display control unit acquires the analysis data 33b stored in the memory 33 as the insertion shape analysis information 33c and calculates the speed ratio of the moving speed of the source coil $C_0$ arranged on the most distal end side of the insertion portion 11 of the endoscope 6 and the moving speed of the source coil $C_{M-1}$ arranged on the most proximal end side of the insertion portion 11 of the endoscope 6 based on the insertion shape analysis information 33c. The analysis result display control block 43 then controls the display condition of the insertion assisting information on the display 28 based on the calculation result.

Next, operations of the biological observation system 1 of the present embodiment will be explained.

When the user inserts the insertion portion 11 of the endoscope 6 from the anus of the examinee into the body cavity, an image of an object located in the body cavity is picked up by the image pickup device 16 provided at the distal end portion 14 of the insertion portion 11. The image of the object picked up by the image pickup device 16 is outputted as an image pickup signal, subjected to signal processing by the video processor 8, converted to a video signal and then outputted to the monitor 9. This causes the image of the object picked up by the image pickup device 16 to be displayed on the monitor 9 as an endoscope observed image.

The endoscope insertion shape detection apparatus 3 detects the magnetic fields emitted from the source coils $C_0$ to $C_{M-1}$ by the sensing coil unit 19 and estimates the insertion shape of the insertion portion 11 based on the detected signals outputted according to the magnetic fields by the shape processing apparatus 21. This causes the insertion shape of the insertion portion 11 estimated by the shape processing apparatus 21 to be displayed on the display 22.

Furthermore, the shape processing apparatus 21 of the endoscope insertion shape detection apparatus 3 sequentially outputs frame data including position information of the respective source coils to the PC 25 of the image processing apparatus 4 via the communication port 21a.

As shown in FIG. 11, the CPU 31 of the PC 25 acquires frame data outputted from the endoscope insertion shape detection apparatus 3 through the frame data acquisition block 41 of the processing program and stores the acquired frame data in the memory 33.

Furthermore, as shown in FIG. 12, the CPU 31 applies analysis processing to the frame data 33a stored in the memory 33 through the analysis processing block 42 of the processing program to thereby generate analysis data 33b having the moving speed of the source coil $C_0$ arranged on the most distal end side of the insertion portion 11 and the moving speed of the source coil $C_{M-1}$ arranged on the most proximal end side of the insertion portion 11 and sequentially stores the generated analysis data 33b in the memory 33. In the present embodiment, suppose the moving speed of the source coil is calculated, for example, from the amount of movement per frame of the source coil. Furthermore, in the present embodiment, suppose the moving speed of the source coil takes a positive value in the direction in which the insertion portion 11 is inserted and a negative value in the direction in which the insertion portion 11 is retracted.

The analysis result display control block 43 acquires latest analysis data out of the analysis data 33b stored in the memory 33 and analysis data immediately preceding the latest analysis data as the insertion shape analysis information 33c at predetermined periods of time (step S201 in FIG. 12).

The analysis result display control block 43 then sets a correction ratio g according to the data of the moving speed of the source coil $C_{M-1}$ arranged on the most proximal end side of the insertion portion 11 of the latest analysis data 33b in the acquired insertion shape analysis information 33c (step S202 in FIG. 12).

To be more specific, the analysis result display control block 43 sets the correction ratio g to 0.75 based on the latest analysis data of the insertion shape analysis information 33c when the moving speed of the source coil $C_{M-1}$ arranged on the most proximal end side of the insertion portion 11 is 20 mm/sec or more. Furthermore, the analysis result display control block 43 sets the correction ratio g to 0.5 based on the latest analysis data of the insertion shape analysis information 33c when the moving speed of the source coil $C_{M-1}$ arranged on the most proximal end side is 0 mm/sec or more and less than 20 mm/sec. Furthermore, the analysis result display control block 43 sets the correction ratio g to 0.25 based on the latest analysis data of the insertion shape analysis information 33c when the moving speed of the source coil $C_{M-1}$ arranged on the most proximal end side is less than 0 mm/sec.

In the present embodiment, the analysis result display control block 43 is configured to acquire latest analysis data out of the analysis data stored in the memory 33 and analysis data immediately preceding the latest analysis data as insertion shape analysis information and set a correction ratio g, but the present invention is not limited to this and the analysis result display control block 43 may also be configured to acquire latest analysis data and P pieces of past analysis data contiguous in time to the latest analysis data as insertion shape analysis information and set a correction ratio g.

Furthermore, in the present embodiment, the analysis result display control block 43 may also acquire any one of information of an angle of curvature of the insertion portion 11, information of a shape pattern of the insertion shape of the insertion portion 11 and information on an amount of insertion of the insertion portion 11 as the insertion shape analysis information 33c and set a correction ratio g (and display period control value Rc, which will be described later).

To be more specific, the analysis result display control block 43 may increase/decrease the correction ratio g according to an increase/decrease of the angle of curvature of the insertion portion 11 (e.g., decreases the correction ratio g as the angle of curvature decreases). Furthermore, the analysis result display control block 43 may also increase/decrease the correction ratio g according to a change of the shape pattern of the insertion shape of the insertion portion 11 (e.g., decreases the correction ratio g as the loop shape is shifted to a quasi-linear shape). Furthermore, the analysis result display control block 43 may also increase/decrease the correction ratio g according to an increase/decrease of the amount of insertion of the insertion portion 11 (e.g., decreases the correction ratio g as the amount of insertion decreases).

The analysis result display control block 43 then calculates a moving speed ratio Rb of the source coils $C_0$ and $C_{M-1}$ in the latest analysis data and a moving speed ratio Rp of the source coils $C_0$ and $C_{M-1}$ in the analysis data immediately preceding the latest analysis data based on the insertion shape analysis information 33c. The analysis result display control block 43 then calculates a display period control value Rc for controlling a display period of the insertion assisting information according to the following expression (4) determined based on the moving speed ratio Rb, moving speed ratio Rp and correction ratio g set in the processing in step S202 in FIG. 12 (step S203 in FIG. 12).

$$Rc = g \times Rb + (1-g) \times Rp \qquad (4)$$

Furthermore, the analysis result display control block 43 compares the display period control value Rc calculated in step S203 in FIG. 12 with a threshold Rcth concerning the display period control value Rc. Upon detecting that the display period control value Rc is greater than the threshold Rcth (step S204 in FIG. 12), the analysis result display control block 43 judges that the insertion portion 11 is inserted or retracted without forming any loop shape or the like and performs processing to erase the insertion assisting information displayed on the display 28 (step S205 in FIG. 12). Furthermore, upon detecting that the display period control value Rc is equal to or less than the threshold Rcth (step S204 in FIG. 12), the analysis result display control block 43 judges that the insertion portion 11 forms a loop shape or the like and the insertion portion 11 has not been correctly inserted, and performs processing to display insertion assisting information on the display 28 (step S206 in FIG. 12).

The insertion assisting information displayed on the display 28 in the present embodiment is, for example, such information indicating stretching of the large intestine, information on a method of canceling the loop shape of the insertion portion 11 that can support the user's operation of inserting the insertion portion 11.

The analysis result display control block 43 then repeats the processing from step S201 to step S206 in FIG. 12 at predetermined periods of time to thereby continue to display insertion assisting information for a period during which the display period control value Rc is equal to or less than the threshold Rcth and erase the insertion assisting information at timing at which the display period control value Rc exceeds the threshold Rcth.

As described above, the biological observation system 1 of the present embodiment has a configuration capable of appropriately changing the display period of insertion assisting information for supporting the user's operation of inserting the insertion portion 11 according to the change of the moving speeds of source coils $C_0$ and $C_{M-1}$. As a result, the biological observation system 1 of the present embodiment appropriately provides insertion assisting information according to the operation on the insertion portion 11 of the endoscope 6, and can thereby reduce the user's uncomfortable feeling compared with the prior arts.

Furthermore, having the aforementioned configuration, the biological observation system 1 of the present embodiment is prevented from displaying the insertion assisting information unnecessarily even when there is a possibility that insertion assisting information may be erroneously displayed, for example, when the user performs instantaneous operation on the insertion portion 11 or when noise is added to the source coils $C_0$ and $C_{M-1}$.

Fourth Embodiment

Figure 13:
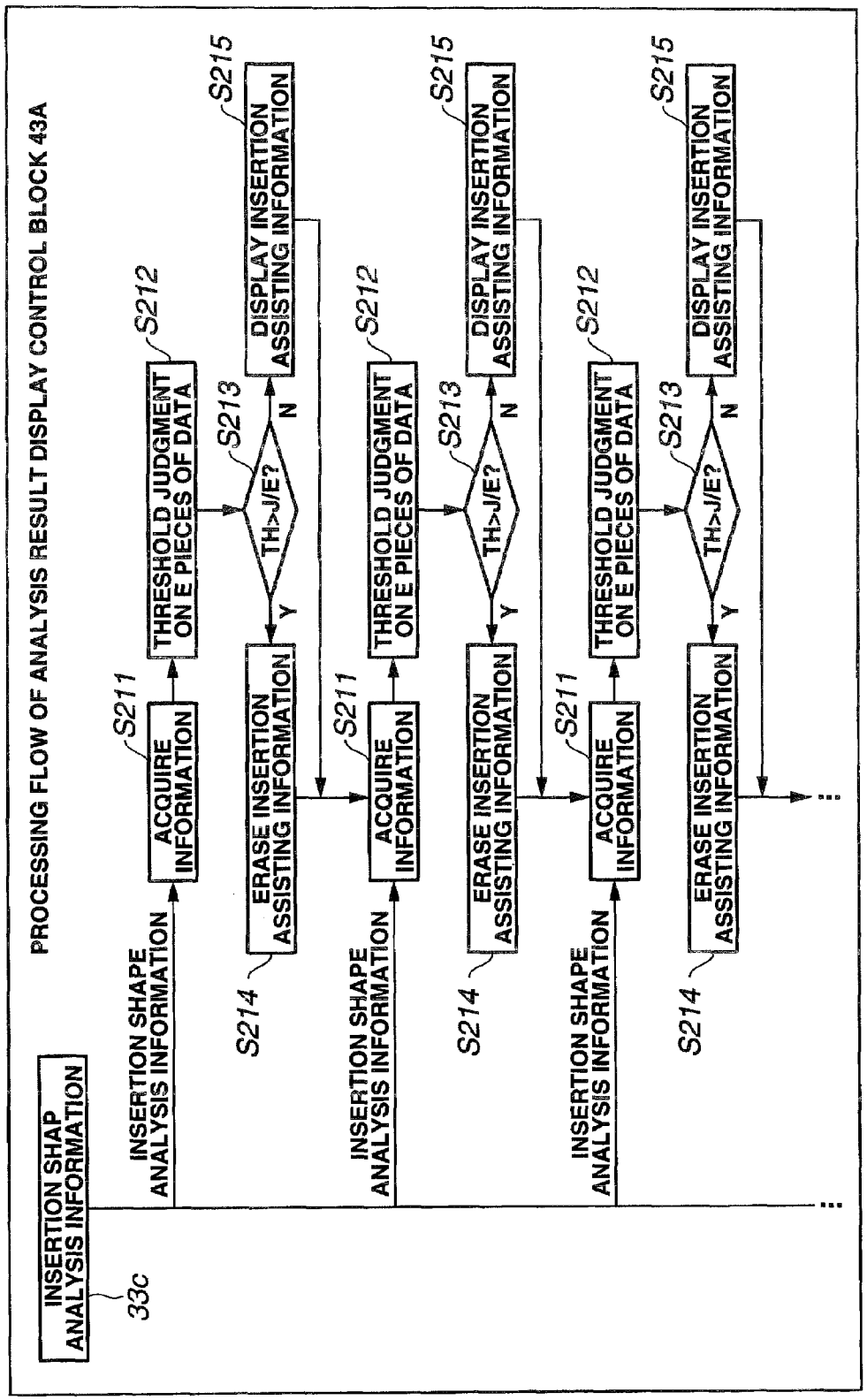
FIG. 13 illustrates a flow of processing performed by an analysis result display control block according to a fourth embodiment of the present invention.

FIG. 13 relates to a fourth embodiment of the present invention. FIG. 13 illustrates a flow of processing performed by the analysis result display control block according to the fourth embodiment of the present invention.

The biological observation system of the fourth embodiment has a configuration substantially the same as that of the biological observation system 1 explained in the first to third embodiments. Therefore, in the present embodiment, suppose explanations of parts having the same configurations or operations as those in the biological observation system 1 of the first to third embodiments will be omitted and explanations will be focused on those having configurations or operations different from those in the biological observation system 1 of the first to third embodiments.

In the CPU 31 (of the biological observation system 1) of the present embodiment, an analysis result display control block 43A of a processing program performs a series of processes which will be described below and which is different from the processing performed by the analysis result display control block 43 of the third embodiment.

The analysis result display control block 43A acquires E pieces (e.g., five pieces) of analysis data combining latest analysis data and one or a plurality of pieces of past analysis data contiguous in time to the latest analysis data out of the analysis data stored in the memory 33 as insertion shape analysis information 33c at predetermined periods of time (step S211 in FIG. 13).

The analysis result display control block 43A then calculates a moving speed ratio of the source coils $C_0$ and $C_{M-1}$ in the acquired E pieces of analysis data and detects J pieces of analysis data for which the calculated moving speed ratio takes a value equal to or less than a predetermined threshold (e.g., 0.1) (step S212 in FIG. 13). The analysis result display control block 43A compares the value of J/E as a display period control value in the present embodiment with a threshold TH (e.g., 0.6). Upon detecting that the value of J/E is smaller than a threshold TH (step S213 in FIG. 13), the analysis result display control block 43A judges that insertion operation or retracting operation has been performed while the insertion portion 11 does not form any loop shape or the like and performs processing for erasing insertion assisting information displayed on the display 28 (step S214 in FIG. 13). Furthermore, upon detecting that the value of J/E is equal to or less than the threshold TH (step S213 in FIG. 13), the analysis result display control block 43A judges that the insertion operation has not been performed appropriately because the insertion portion 11 forms a loop shape or the like and performs processing to display the insertion assisting information on the display 28 (step S215 in FIG. 13).

The analysis result display control block 43A then repeatedly performs the processing from step S211 to step S215 in FIG. 13 at predetermined periods of time, thereby continues to display insertion assisting information for a period during which the value of J/E is equal to or less than the threshold TH and erases the insertion assisting information at timing at which the value of J/E exceeds the threshold TH.

As described above, the biological observation system 1 of the present embodiment has a configuration capable of appropriately changing the display period of insertion assisting information for supporting the user's operation of inserting the insertion portion 11 according to the change of the moving speeds of the source coils $C_0$ and $C_{M-1}$. As a result, the biological observation system 1 of the present embodiment appropriately provides insertion assisting information according to the operation on the insertion portion 11 of the endoscope 6, and can thereby reduce the user's uncomfortable feeling compared with the prior arts.

Furthermore, having the aforementioned configuration, the biological observation system 1 of the present embodiment is prevented from displaying the insertion assisting information unnecessarily even when there is a possibility that insertion assisting information may be erroneously displayed, for example, when the user performs instantaneous operation on the insertion portion 11 or when noise is added to the source coils $C_0$ and $C_{M-1}$.

The present invention is not limited to the above described embodiments and it goes without saying that the present invention can be modified or applied in various ways without departing from the spirit and scope of the invention.

What is claimed is:

1. An endoscope insertion shape analysis system including a processor, the system comprising:
   an insertion state acquisition unit configured to acquire coordinate values of a plurality of locations in an insertion portion of an endoscope inserted in an examinee;
   an insertion shape detection unit configured to detect, when a distance between coordinate values of arbitrary two locations selected among the coordinate values at the plurality of locations is less than a predetermined value, an insertion shape of the insertion portion between the two locations;
   a coordinate plane setting unit configured to set a plurality of coordinate planes according to coordinate values determined based upon a divided line segment between the two locations and the insertion shape detected by the insertion shape detection unit, the plurality of coordinate planes including a first coordinate plane on which the insertion shape detected by the insertion shape detection unit exist having a first normal vector, and a second coordinate plane having a second normal vector acquired by tilting the first normal vector by a predetermined angle with respect to the first coordinate plane;
   an insertion shape projecting unit configured to project the insertion shape detected by the insertion shape detection unit onto each of the plurality of coordinate planes; and
   an insertion shape judging unit configured to acquire a judgment result indicating that a predetermined shape exists in the insertion shape detected by the insertion shape detection unit, when the predetermined shape is detected in all of the insertion shapes projected onto the plurality of coordinate planes.

2. The endoscope insertion shape analysis system according to claim 1, wherein the plurality of coordinate planes includes the first coordinate plane, the second coordinate plane, and a third coordinate plane having a third normal vector acquired by three-dimensionally rotating the second normal vector in a state where the predetermined angle is maintained with respect to the first normal vector.

3. The endoscope insertion shape analysis system according to claim 2, wherein the predetermined shape is a loop shape.

4. The endoscope insertion shape analysis system according to claim 3, wherein the insertion shape judging unit includes a feature value calculation unit configured to calculate a feature value for each of the insertion shapes that were projected on the plurality of coordinate planes, and
   the insertion shape judging unit judges whether or not the predetermined shape exists on the insertion shape detected by the insertion shape detection unit by comparing a preacquired value with the feature value for each of the insertion shapes calculated by the feature value calculation unit.

5. The endoscope insertion shape analysis system according to claim 4, wherein the feature value is a power spectrum calculated based on a loop shape acquired in advance and a coordinate value of the insertion shape.

6. The endoscope insertion shape analysis system according to claim 4, wherein when the predetermined shape does not exist on any one of the projected shapes on each of the plurality of coordinate planes, a different arbitrary combination of locations is selected.

* * * * *